(12) United States Patent
Konstantino et al.

(10) Patent No.: US 11,213,296 B2
(45) Date of Patent: *Jan. 4, 2022

(54) DEVICES AND METHODS FOR RESHAPING BLOOD VESSELS

(71) Applicant: Sano V Pte Ltd, Singapore (SG)

(72) Inventors: Eitan Konstantino, Orinda, CA (US); Gary Binyamin, Berkeley, CA (US); Steven Wiesner, Singapore (SG); Li Min Koh, Singapore (SG)

(73) Assignee: Sano V Pte Ltd, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/189,947

(22) Filed: Nov. 13, 2018

(65) Prior Publication Data

US 2019/0076151 A1    Mar. 14, 2019

Related U.S. Application Data

(63) Continuation of application No. 15/905,415, filed on Feb. 26, 2018, now Pat. No. 10,499,923, which is a
(Continued)

(51) Int. Cl.
*A61B 17/12*      (2006.01)
*A61B 17/064*    (2006.01)
(Continued)

(52) U.S. Cl.
CPC ...... *A61B 17/12109* (2013.01); *A61B 17/068* (2013.01); *A61B 17/0644* (2013.01);
(Continued)

(58) Field of Classification Search
CPC ........ A61B 17/12109; A61B 17/12145; A61B 2017/0427; A61B 2017/0437; A61F 2/2475; A61F 2/26
See application file for complete search history.

(56) References Cited

U.S. PATENT DOCUMENTS 8,240,313 B2    8/2012  Hsu
9,918,719 B2    3/2018  Konstantino et al.
(Continued)

FOREIGN PATENT DOCUMENTS

JP    2003512128 A    4/2003
JP    2014508571 A    4/2014
(Continued)

OTHER PUBLICATIONS

"Extended European Search Report and Search Opinion dated Nov. 17, 2017 for European Patent Application No. EP15805768.7".
(Continued)

*Primary Examiner* — Carrie R Dorna
(74) *Attorney, Agent, or Firm* — Wilson Sonsini Goodrich & Rosati

(57) ABSTRACT

Veins and other blood vessels may be reshaped by introducing an implant through the vessel walls with anchors positioned on opposite sides of the wall. The anchors typically include an elongate body having coils or other anchors formed therein. The implants may be delivered percutaneously using a cannula which can hold the anchor externally or internally. The methods and devices are useful in treating a dorsal vein to reduce blood flow in patients suffering from erectile dysfunction.

12 Claims, 9 Drawing Sheets

Related U.S. Application Data continuation of application No. 14/732,629, filed on Jun. 5, 2015, now Pat. No. 9,918,719.

(60) Provisional application No. 62/009,267, filed on Jun. 8, 2014.

(51) Int. Cl.
| | |
|---|---|
| *A61F 2/26* | (2006.01) |
| *A61F 2/24* | (2006.01) |
| *A61B 17/068* | (2006.01) |
| *A61F 5/41* | (2006.01) |
| *A61B 17/00* | (2006.01) |
| *A61B 17/04* | (2006.01) |
| *A61B 17/06* | (2006.01) |
| *A61F 2/06* | (2013.01) |

(52) U.S. Cl.
CPC ........ *A61B 17/12* (2013.01); *A61B 17/12036* (2013.01); *A61B 17/12145* (2013.01); *A61F 2/26* (2013.01); *A61F 5/41* (2013.01); *A61B 2017/00778* (2013.01); *A61B 2017/00867* (2013.01); *A61B 2017/0406* (2013.01); *A61B 2017/0409* (2013.01); *A61B 2017/0417* (2013.01); *A61B 2017/0419* (2013.01); *A61B 2017/0443* (2013.01); *A61B 2017/0464* (2013.01); *A61B 2017/0649* (2013.01); *A61B 2017/06052* (2013.01); *A61B 2017/06171* (2013.01); *A61F 2/2442* (2013.01); *A61F 2/2475* (2013.01); *A61F 2002/068* (2013.01); *A61F 2220/0008* (2013.01)

(56) References Cited

U.S. PATENT DOCUMENTS

| | | | |
|---|---|---|---|
| 2003/0078465 A1 | 4/2003 | Pai et al. | |
| 2003/0209835 A1* | 11/2003 | Chun | A61L 27/34 |
| | | | 264/339 |
| 2004/0111100 A1 | 6/2004 | Benderev et al. | |
| 2004/0117004 A1* | 6/2004 | Osborne | A61F 2/07 |
| | | | 623/1.36 |
| 2004/0122474 A1 | 6/2004 | Gellman et al. | |
| 2005/0277907 A1 | 12/2005 | Jackson | |
| 2007/0112423 A1 | 5/2007 | Chu | |
| 2008/0215072 A1 | 9/2008 | Kelly | |
| 2008/0319256 A1 | 12/2008 | Mortier et al. | |
| 2010/0256661 A1 | 10/2010 | Brandeis | |
| 2011/0007458 A1 | 1/2011 | Liao et al. | |
| 2011/0066254 A1 | 3/2011 | Forsell | |
| 2013/0245534 A1 | 9/2013 | Miller et al. | |
| 2018/0177506 A1 | 6/2018 | Konstantino et al. | |

FOREIGN PATENT DOCUMENTS

| | | |
|---|---|---|
| WO | WO-9311823 A1 | 6/1993 |
| WO | WO-2012097086 A1 | 7/2012 |
| WO | WO-2013151712 A1 | 10/2013 |
| WO | WO-2013152283 A1 | 10/2013 |
| WO | WO-2013179137 A3 | 3/2014 |
| WO | WO-2015191465 A1 | 12/2015 |

OTHER PUBLICATIONS

"Final Office action dated Feb. 4, 2019 for U.S. Appl. No. 15/905,415".
"Singapore Search Report and Written Opinion dated Nov. 24, 2017 for SG Patent Application No. 11201610295P".
"International search report and written opinion dated Nov. 10, 2015 for PCT/US2015/034720."
"Notice of Allowance dated Jan. 8, 2018 for U.S. Appl. No. 14/732,629".
"Office action dated Jul. 21, 2017 for U.S. Appl. No. 14/732,629".
Office action dated Jan. 17, 2017 for U.S. Appl. No. 14/732,629.
RAO; et al., "Vasculogenic impotence. Arterial and venous surgery. Urol Clin North Am. May 2001;28(2):309-19."
Notice of Allowance dated Feb. 14, 2018 for U.S. Appl. No. 14/732,629.
U.S. Appl. No. 15/905,415 Office Action dated May 18, 2018.
Notice of allowance dated Aug. 12, 2019 for U.S. Appl. No. 15/905,415.

* cited by examiner

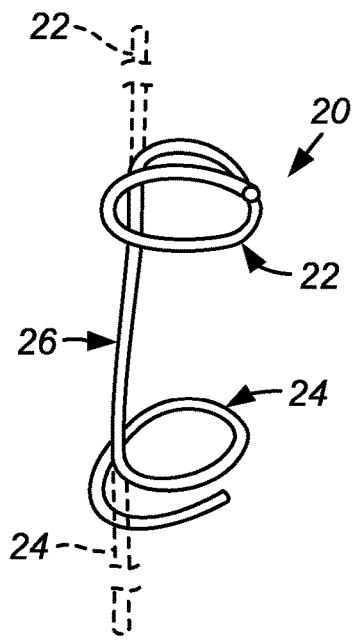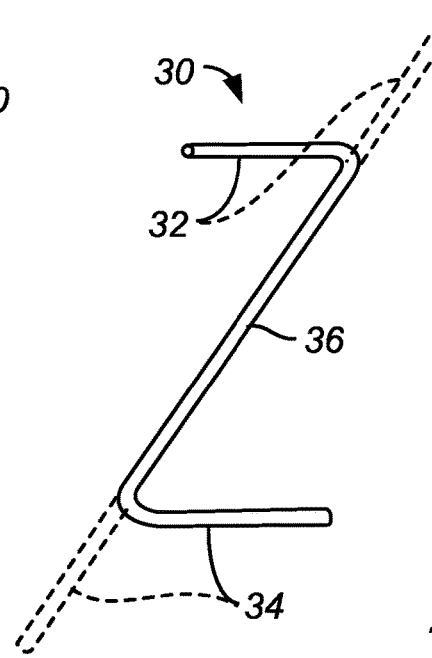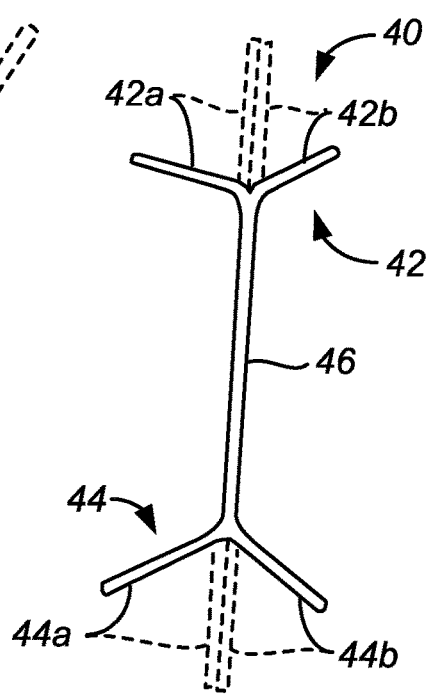
FIG. 3A  FIG. 3B  FIG. 3C
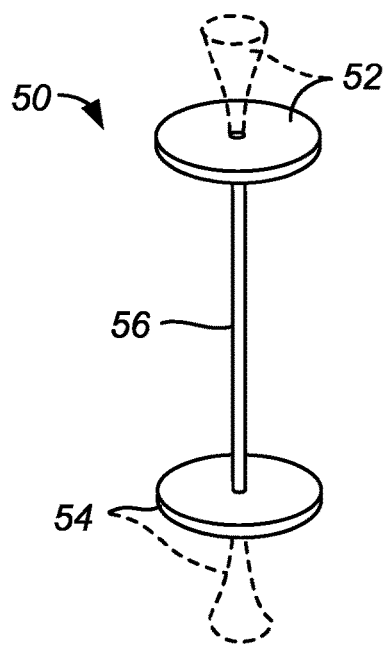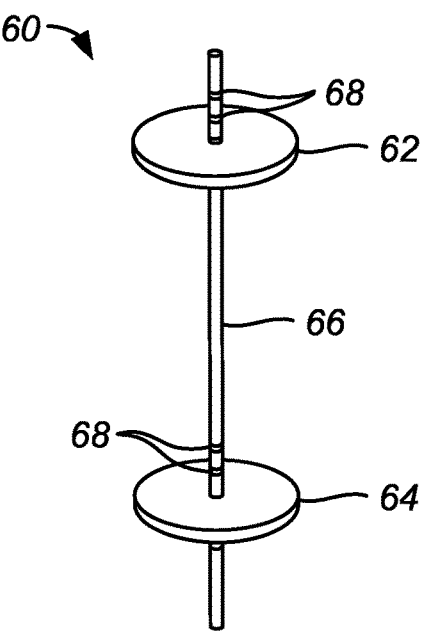
FIG. 3D  FIG. 3E

DEVICES AND METHODS FOR RESHAPING BLOOD VESSELS

CROSS-REFERENCE TO RELATED APPLICATION

This application is a continuation of U.S. patent application Ser. No. 15/905,415, filed Feb. 26, 2018, which is a continuation of U.S. patent application Ser. No. 14/732,629, filed Jun. 5, 2015, now U.S. Pat. No. 9,918,719, which claims the benefit of Provisional Application No. 62/009,267, filed on Jun. 8, 2014, the full disclosure of which is incorporated herein by reference.

BACKGROUND OF THE INVENTION

1. Field of the Invention

The present invention relates to system and method for treating biological vessels and more particularly reshaping veins and to modify their biomechanics in order to allow a reduction in blood flow in response to an increase in surrounding blood pressure to modulate flow modulation.

Venous leaks include various phenomenon where changes in or around the venous system cause a noticeable clinical impact. For example, the veins have internal valves that prevent back flow and allow blood flow back to the heart in the low pressure venous system. Vascular leaks may occur as a vein diameter increases around which can inhibit valve closure (causing a venous leak). Such venous leaks may cause an accumulation of blood in the lower extremities that in turn may cause discomfort and pain. It is desirable to be able to reshape the vein with the goal of restoring the functionality of the valve.

Venous valving also play an important role in penile erection. Penile erection results from increased local blood pressure in the penis. Two corpora cavernosa located in the penis fill with blood coming from the deep arteries of the penis. Expansion of the corpora cavernosa compresses the associated outflow veins, thus inhibiting the blood outflow and allowing the increased local blood pressure to cause an erection.

In a large percentage of men over age 40, this functionality is impaired, commonly referred to as erectile dysfunction (ED). While the cause can be an insufficient inflow of blood (arteriogenic ED) in many cases the cause is the incomplete inhibition of venous outflow (venogenic ED). Incomplete venous occlusion typically results from changes in the biomechanical behavior of the veins that increase resistance to pressure.

Presently, ED has limited treatment options. Available medications typically increase blood inflow and may not be effective in men suffering from venous leak. Other treatment options usually involve a major surgery and complete occlusion of major vein, but such treatments suffer from poor long term outcomes. The failure of complete venous occlusion is believed to be caused by the development of collateral veins in response to complete occlusion of the deep dorsal vein and/or other penile veins.

For these reasons, it would be desirable to provide procedures and devices with improved short term and/or long term results for treating ED and modulating flow through other veins. It would further be desirable to provide devices for inhibiting venous flow which may be implanted in relatively simple procedure, particularly outpatient procedures and procedures that can be performed in a doctor's office with local or no anesthesia. At least some of these objectives will be met by the inventions described hereinafter.

2. Description of the Background Art

Methods and devices for treating ED and for modulating blood flow through veins and arteries are described in US Patent Publs. 2005/0277907; 2011/0066254; and 2011/007458; and U.S. Pat. No. 8,240,313. See also Rao and Donatucci (2001) Urologic Clinics 28:309-319.

SUMMARY OF THE INVENTION

The present provides methods and devices for inhibiting blood flow through a patient's vasculature, particularly through veins but also finding use in arterial flow. The methods rely on placing an implant through a wall of the blood vessel so that anchors on opposite ends of the implant will draw the walls of the vessel together which will reshape or reconfigure a shape of the blood vessel lumen. Often, the reshaped lumen will become more oval than the native lumen. In other instances, the new shape will resemble a figure eight or a bow tie. In still other embodiments, one side of the lumen can be closed to reduce the area of the vessel lumen without necessarily changing the shape which may remain generally circular.

In a first aspect, a method according to the present invention for inhibiting blood flow through a vein comprises penetrating an implant inwardly through a proximal location on a wall of the vein. The implant is further penetrated outwardly through a distal location on the wall of the vein. The distal end of the implant is anchored on the exterior surface of the wall adjacent to the distal location, and similarly a proximal end of the implant is anchored on the exterior surface of the wall adjacent to the proximal location. The anchored ends of the implant are responsible for reshaping the lumen of the veins between the first and second locations which in turn results in blood flow inhibition.

In an exemplary embodiment, penetrating may comprise advancing a cannula through the proximal and distal locations on the wall, where the implant is carried over a distal region from the cannula. Typically, the implant will comprise an elongate member, such as a wire or ribbon, coiled over the distal region of the cannula. In such instances, anchoring the distal end of the elongate member may comprise releasing the distal end after said distal end is positioned over the exterior surface of the wall adjacent to the distal end. Anchoring of the proximal end will typically comprise releasing the proximal end of the elongate member after the distal end has been released and after the proximal end has been positioned at a preselected distance from the distal end. Alternatively, anchoring the proximal end of the implant may comprise releasing the proximal end after the proximal end is positioned over the exterior surface of the wall adjacent to the proximal location. In such cases, anchoring the distal end of the implant will comprise releasing the distal end after the proximal end has been released and after the distal end has been positioned at a preselected distance from the proximal end.

In an alternative embodiment, the penetrating may comprise advancing a cannula through the proximal and distal locations on the wall, where the implant is constrained within an interior, typically a lumen or other passageway, of the cannula. In such cases, the implant typically comprises an elongate member having a distal end pre-shaped into a distal anchor and a proximal end pre-shaped into a proximal anchor. The elongate member is in a straightened configuration when constrained within the interior of the cannula, i.e. the pre-shaped anchors are both in a straightened configuration. Anchoring the distal end of the elongate member thus comprises advancing the distal end from the cannula so that it assumes an anchor configuration over the exterior surface of the wall adjacent to the distal location. Similarly, anchoring the proximal end of the elongate member typically comprises releasing the proximal end from the cannula so that it assumes an anchor configuration over the exterior surface of the wall adjacent to the proximal location. The distal end of the elongate member is advanced by advancing a pusher within the passageway cannula against a proximal end of the elongate member, and the proximal end of the elongate member is released by retracting the cannula over said proximal end while it remains engaged against the pusher.

While these methods may be utilized for delivering the implants of the present invention into a variety of veins and other blood vessels, the methods may find their greatest use in delivering the implants to a dorsal vein to treat a patient suffering from erectile dysfunction.

In a second aspect of the present invention, the present invention provides implants for inhibiting blood flow through a vein or other blood vessel. The implant typically comprises an elastic, elongate member having a distal end and a proximal end. The distal and proximal ends are each pre-shaped to assume a delivery configuration when constrained and an anchor configuration when unconstrained. The distal and proximal ends, when in their anchor configurations, are separated by a middle region which controls the distance between opposed walls of a vein when the implant is implanted in the vein with each anchor on an exterior surface of a wall of the vein. While the distal and proximal ends will usually have similar geometries, they can also have different geometries, a number of which are illustrated in detail below.

The implants of the present invention will typically comprise an elongate member comprising a wire (or in some cases a ribbon) having a coiled distal end and a coiled proximal end separated by a straight middle region. The elongate member may alternatively comprise a wire or ribbon having a deflected distal end and a deflected proximal end, e.g. in the shape of an L or J. In still other embodiments, an elongate member may have an adjustable anchor at each end, e.g. a flange, a cap, or other structure which may be adjusted on a ratcheted surface of the elongate member. In still other embodiments, each end of the elongate member may be split, forked, or bifurcated to spread open upon release from constraint. In still further embodiments, each end of the elongate member may have a collapsible disc or other collapsible anchor structure fixed to a central region. In at least most cases, the anchor regions of the implants will be deformable or reconfigurable so that they can be placed in a low profile configuration for delivery and then expanded into their anchoring configuration when the anchors are exterior to the blood vessel.

The present invention still further provides implant delivery systems for the implants just described. The delivery systems will usually comprise the implant in combination with a delivery catheter configured to penetrate opposite walls of a vein. The delivery systems will be configured to carry the implant, in a constrained configuration. across the vein or other blood vessel walls, and to release the implant so that the distal anchor is positioned against an external surface of a distal side on the wall and the proximal anchor is positioned against an external surface of a proximal side on the wall.

In a first embodiment, the cannula of the implant delivery system of the present invention comprises an inner needle and an outer mandrel. The distal end of the elongate member of the implant is removably secured to the needle, and the proximal end of the elongate member of the implant is removably secured to the mandrel. In this way, rotation of the needle relative to the mandrel in a first direction coils the elongate member more tightly over the cannula and rotation of the needle in an opposite direction releases the elongate member from the cannula.

In a second embodiment, the cannula of the implant delivery system comprises a hollow body and a pusher disposed in a lumen of the hollow body. The implant is constrained in a straight configuration when present in the lumen of the cannula body, and the implant is released from the cannula body by advancing the pusher in the lumen relative to the catheter body. A distal end of the implant will thus be released first from the needle on a distal side of the target vein or other blood vessel. After deploying the distal anchor on the distal side of the vein, the needle may be retracted proximally to deploy the proximal anchor on a proximal side of the vein.

BRIEF DESCRIPTION OF THE DRAWINGS

FIG. 2A shows the blood vessel without an implant and FIGS. 2B-2E show different implants and placements.

FIGS. 3A-3E different implant designs in accordance with the principles of the present invention.

DETAILED DESCRIPTION OF THE INVENTION

Figure 1:
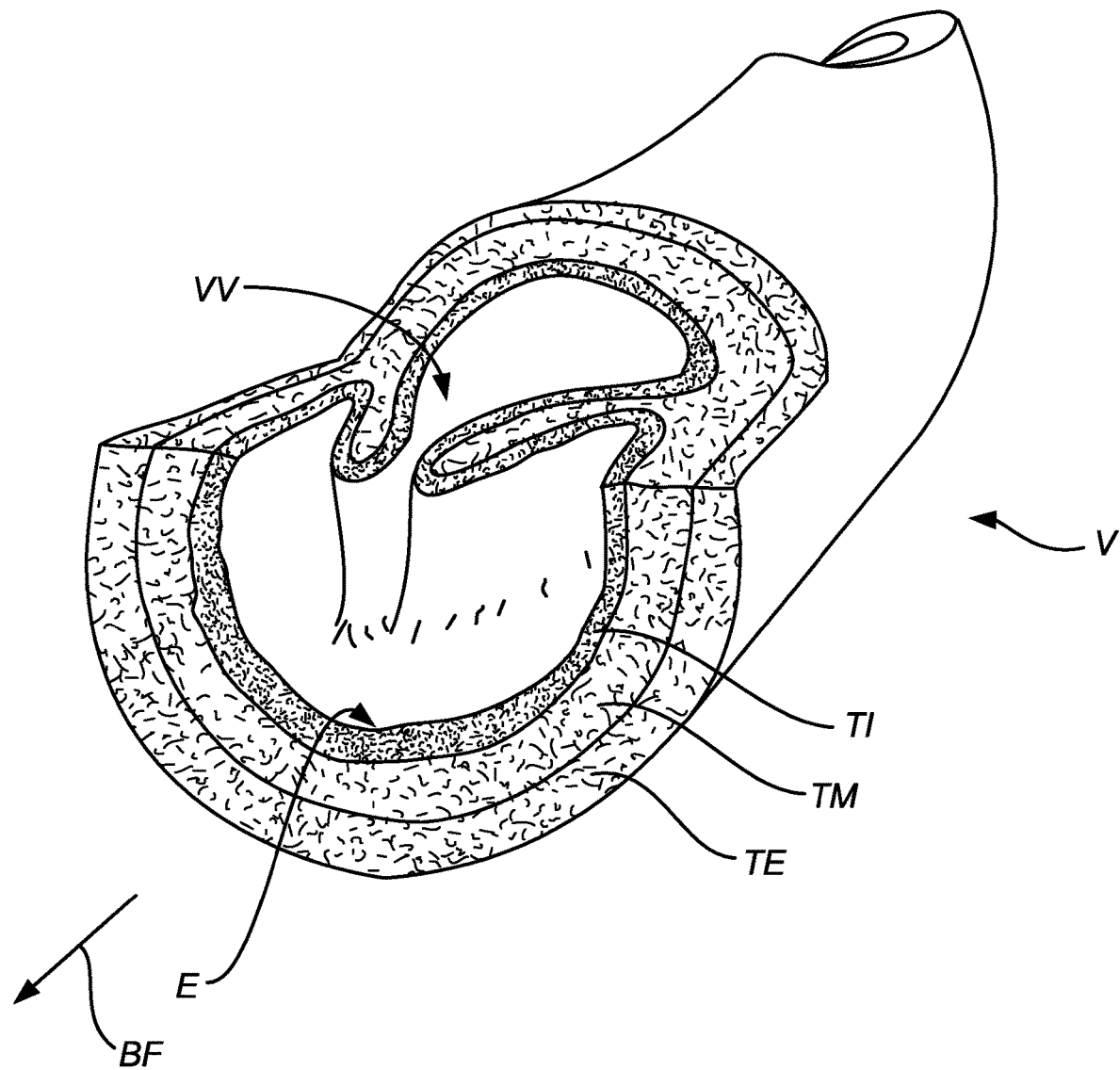
FIG. 1 shows a general image of blood vessel.

The present invention provides an implant for reshaping veins and other blood vessels in order to change their biomechanical behavior without blocking flow, typically inhibiting venous flow to treat conditions such as erectile dysfunction (ED). The implant has a low profile, is self-conforming to the vein, can be made out of metal or polymer, and can be delivered to the body using a delivery system. The implant is typically introduced through a venous or other blood vessel wall using a percutaneous delivery method, typically by penetrating a delivery cannula though the vein to place anchors on the implant on distal and proximal external surfaces of the blood vessel wall. Once released from its delivery system, the implant collapses or otherwise reconfigures to engage opposed outer surfaces of the vessel wall and to draw the surfaces together. External remodeling of the vessel wall will necessarily reconfigure the lumen reducing blood flow through the vessel The implant is not intended to block blood flow.

In one embodiment, the implant comprises of a combination of intravascular and extra vascular elements. The implant can be delivered using a delivery system by piercing the vessel wall. The delivery system, or the implant, or both, pierce the vessel wall at least once in order to implant the device. The implant is initially constrained by the delivery system and, upon release from the delivery system, the implant assumes its free shape which will reshape of the vessel without blocking the blood flow. The implant is anchored at at least one location that can be inside or outside the vessel wall, usually being anchored at two locations on opposite external surface locations adjacent to where the vessel has been pierced by the delivery tool. Upon release, the implant forces the vessel to change its shape from an approximately cylindrical shape to an oval or less cylindrical shape than the original shape of the vessel, e.g. an oval shape or "bow tie" shape. In some cases it can be a cylindrical shape with a reduced diameter.

The shape change increases the ability of the vessel to collapse or to further change its shape under external forces or pressures at least in one direction. The implant changes the biomechanics of the vessel in the treated area by modifying the moment of inertia to make the vessel more prone to bending or compressing. While the shape change could lead to some immediate decrease in blood flow inside the vessel, blood flow is not blocked. When external forces or surroundings blood pressure increases and affects the vessel, further decrease in blood flow or even a temporary stop of blood flow will take place compared to the normal or non-impacted state. The implant may be placed in the vessel temporarily or permanently depending on the patient's needs as determined by the physician.

In a first embodiment the implant is made of an elastic metal such as a stainless steel alloy, a cobalt based alloys, or a nickel titanium alloy. The implant can also be made of polymer, such as nylon, polyurethane, a silk-based polymer, or other known polymers. The implant can be straightened to a low profile shape and constrained in a needle type delivery system. The needle may be used to pierce a superficial target vessel (such as the dorsal vein for the treatment of ED), allowing for release of the implant inside the blood vessel. Once released, the implant assumes its free shape. When anchored in one or two locations adjacent to the vessel wall, or externally to the vessel, the implant changes its shape and/or reduces its length from the original constrained shape, causing the vessel to change shapes, e.g., become more oval which makes the vessel more prone to collapsing or compressing in the direction of its short axis. Under external forces (manual compression or increase in blood flow in the area) the blood flow in this vessel will decrease is inserted.

In another embodiment, the implant may be formed from a wire, a ribbon, or other elongate body having a free shape that preferably includes a middle or central portion that will have a low profile when present in the blood vessel lumen. Such a central portion is usually linear, may alternatively have an S- or a C-shape, but can also follow a serpentine or meandering line. The implant has one end region in which the general linear shape of the center portion changes in order to create an extra vascular anchoring point that will be larger or different in shape from the piercing hole of the vessel in a manner that will keep its end portion externally to the vessel. The implant has another end portion that can be anchored externally to the vessel in a generally opposing side of the vessel or down or upstream from the first entry point of the implant. The free size of the implant intravascular portion is smaller than the original diameter of the vessel in this area hence decreasing the vessel diameter along the axis of the implant with an end result of making the vessel oval in shape.

In another embodiment the implant may a central elongate region and separate end caps or anchors at each end that are positioned externally on the vessel.

In one specific example, the implant can be used to reshape a superficial vein of 2 mm diameter. In this case the implant will be used to decrease the diameter of the implant along the axis generally exist between the entry hole and the exit hole of the implant from the vessel from 2 mm to at least 1.8 mm, 1.5 mm or 1 mm or 0.5 mm or until both walls of the vessel will come into contact crating a ridge that limits the flow in this area but without blocking the flow in the blood vessel. Generally the implant will be used to "ovalize" the vessel by creating an at least 10% size difference and sometimes an at least 15% difference between a long diameter and a short diameter of the vessel cross section in the area where the implant.

In another example for a 3 mm vein, the implant length can be 2.5 mm consisting of a generally linear center portion with end regions to anchor the implant in one or two opposing sides of the vessel. This implant can be straightened to a linear wire constrained and stored, pre-loaded, in a small gauge needle. When straightened the wire length of the implant can be as long as 5 mm or even 10 mm depending on the anchor shape and design. The anchors can have a spiral design, typically having at least one coil, often have more than one coil, to keep the end of the implant anchored external to the vein. The distal end of the implant can be extravascularly released, embedding an anchor further away from the delivery system. As the delivery system retracts the implant proximal end will be release out of the vein forming a spring like shape compressing the vein into an oval shape. In this case only the central implant portion is released inside the vessel with minimal footprint exposed to blood flow.

The implant can be made from a metal or polymer wire or other elongate member. Exemplary wire thicknesses are as small as 10 micron or as large as 1 mm. Typical ranges are 10 microns to 1 mm, 20 microns to 0.5 mm, and 30 microns to 0.1 mm. For treatment of the dorsal vein, the implant will typically be at the smaller end of the size ranges. The central portion of the implant has a length that is smaller than the diameter of the vessel to be treated, and the full wire length prior to anchor deployment will usually be longer or even a lot longer than the diameter of the vessel. It is desirable that the footprint of the implant in the area exposed to blood flow will be minimal or covered with tissue to minimize thrombus formation in the vessel. Anti-thrombotic surface finishes or coatings may also be used.

In one embodiment, the implant is formed from a shape memory material, such as a nickel titanium alloy or a shape memory polymer, that reassumes its free shape in response to a change in temperature or by inducing electrical field or energy field. For small, superficial or semi-superficial vessels, the implant can be delivered through a small gauge needle or a small diameter extra vascular delivery system. External guiding such as ultrasonic transducers or imaging or other known methods can be used to guide the delivery system to the target vessel. In other embodiments, the implant will be formed from a material that relies on the super elastic propertied to expand in response to a release from constraint.

Referring to FIG. 1, a typical vein V comprises a tubular vessel having an outer tunica externa TE, a tunica media TM, and a tunica interna TI. The inner wall of the tunica interna intern is covered with endothelium E. Veins are also characterized by venous valves VV which allow blood to flow in the direction of arrow VF back toward the heart while preventing blood flow away from the heart. In older individuals, the function of the venous valves can sometimes be compromised, and the methods and devices of the present invention may be particularly useful for improving valvular performance in such comprised veins. For example, in patients suffering from erectile dysfunction, the devices and methods of the present invention may be used to improve such venous function, particularly in a dorsal vein as described in detail below.

Figure 2A:
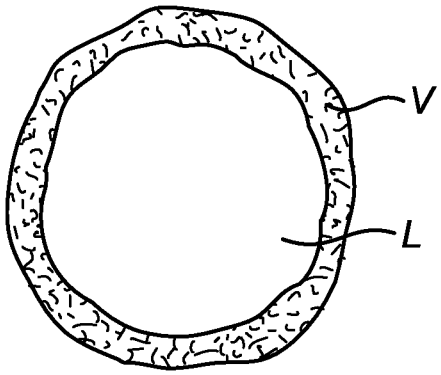
FIGS. 2A-2F shows transverse cross-sections of a blood vessel.
Figure 2B:
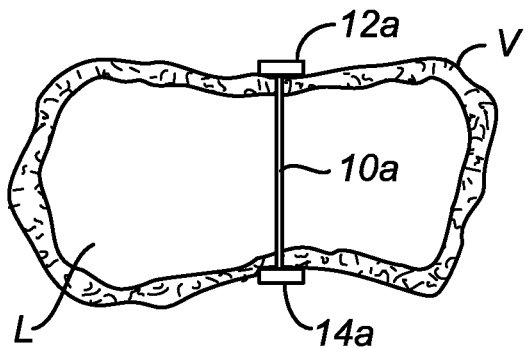

Referring now to FIGS. 2A though 2F, placement of a number of exemplary implants can in a vein V will be described. A native vein V, prior to implantation of an implant according to the present invention, is illustrated in FIG. 2A. Vein V has a generally circular lumen L. As shown in FIG. 2B, the vein may be deformed to a generally ovoid or rectangular configuration by placement of a first implant 10a having a distal anchor 12a and a proximal anchor 14a on the exterior surfaces of the vein. A central region of the implant between the anchors 12a and 14a has a length selected which is less than that of diameter of the unconstrained vein, as shown in FIG. 2A. Thus, placement of the anchor will draw the opposed locations on the wall together creating the desired remodeling or reshaping of the vessel and the lumen.

Figure 2C:
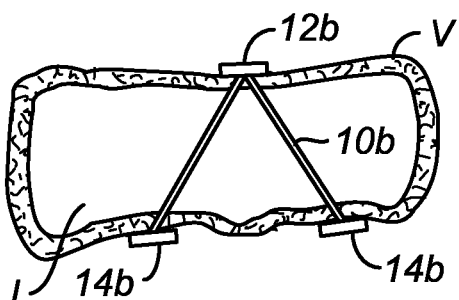

An alternative implant 10b having two central regions is illustrated in FIG. 2C. The deformation of the vessel wall is shown to be generally the same as that in FIG. 2B, but it will be appreciated that by using different divergence angles and different leg lengths on the implant, the geometry of the deformed vessel can be controlled.

Figure 2D:
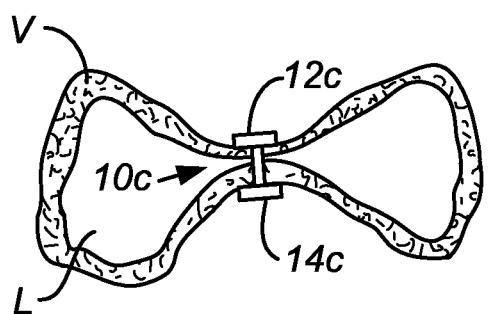

Referring now to FIG. 2D, use of an implant 10C having a much shorter central portion will cause the opposed wall locations of the vein V to more fully collapse, resulting in a figure eight or bow tie cross section for the vessel.

Figure 2E:
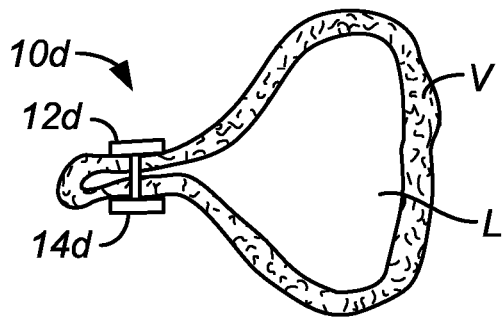

Referring now to FIG. 2E, in implant 10D similar dimensions to implant 10C can be offset toward one side of the vessel, resulting in a partial closing off of only a portion of the vessel lumen, leaving the other side of the vessel open but much smaller than the lumen of the native vessel.

Figure 2F:
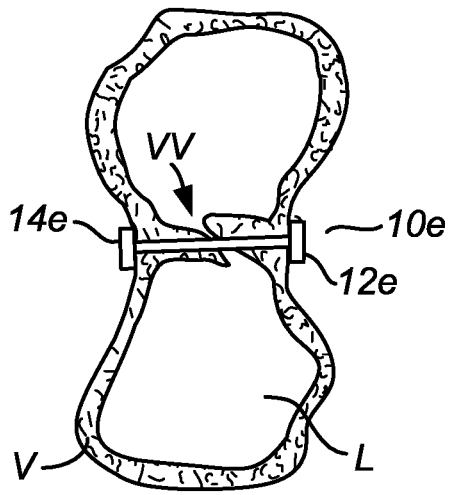

Referring to now FIG. 2F, in implant 10E can be placed through a vinous wall through a region of the vein having a valve VV present.

Figure 2G:
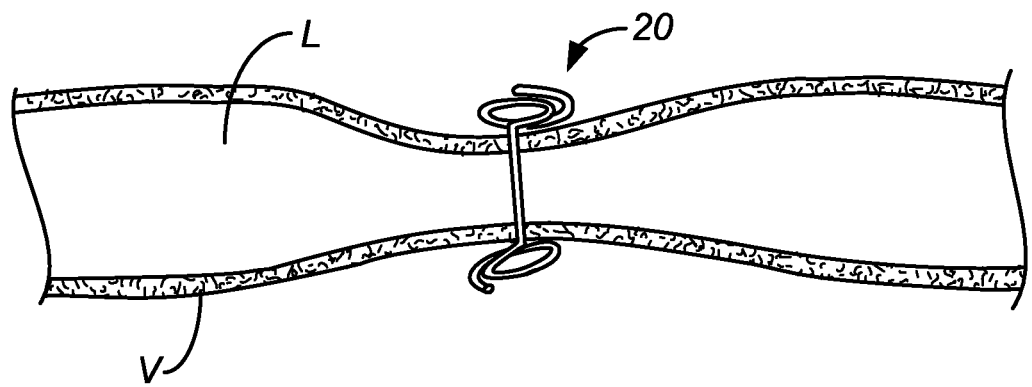
FIGS. 2G and 2H show longitudinal cross-sections of a blood vessel with one implant (FIG. 2G) and two implants (FIG. 2H).
Figure 2H:
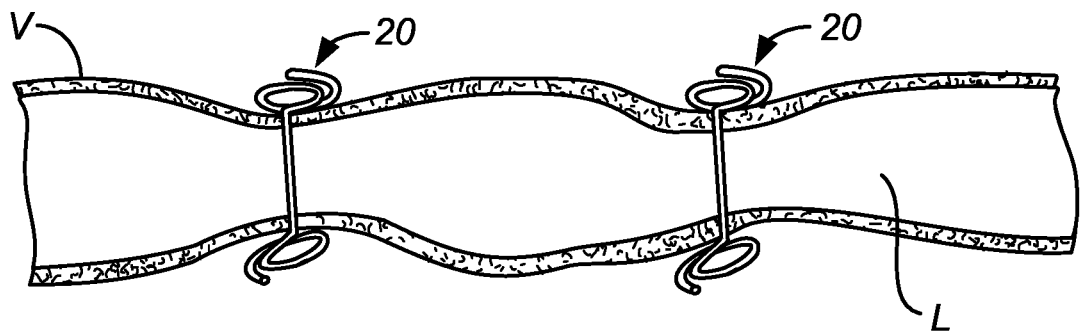

Referring now to FIGS. 2G and 2H, implants 20, having coiled ends as described more fully below, may be placed at a single location as shown in FIG. 2G or at two or more longitudinally displaced locations, as shown in FIG. 2H.

Referring now to FIG. 3A, a variety of specific designs for different implants constructed in accordance with the principals of the present invention will be described. The coil implant 20 is shown in some detail in FIG. 3A. The coil implant 20 will usually consist of a single elastic elongate member having a distal coil 22 pre-formed at a distal end thereof and a proximal coil 24 pre-formed in a proximal end thereof. The elongate member will typically be a wire, more typically being a metal wire formed from an elastic or super elastic metal alloy as described above. Alternatively, the elongate member could have other geometric forms, such as being a ribbon, a small diameter helix, (where the coils at each end would be a second geometric feature with a much larger diameter than the helical diameter). The elongate member could also be formed from a polymer, typically an elastic polymer and more typically a super elastic polymer, as is known in the art. The dimensions of the coil implant 20, including the diameters of the proximal and distal coils 22 and 24, as well as the distance between the proximal and distal coils, will be selected based upon the target blood vessel. Specific dimensions useful for the dorsal vein are provided hereinafter. The coils 22 and 24 are joined by a middle or central region 26 which is generally integrated with the coil portions (i.e. the entire coil implant is formed from a single continuous body of material), where the middle portion 26 will define the length between the coil portions. Although shown as a straight segment, the middle portion 26 may be curved, serpentine, zig-zag, or have other secondary geometry, but generally a straight profile with minimal "footprint" to disturb blood flow will be preferred.

A Z-implant 30 is illustrated in FIG. 3B. The Z-implant will also typically be formed from a single elongate member, typically a wire or a ribbon, having a distal leg 32 and a proximal leg 34 pre-formed therein. Each of the legs will be inclined or deflected relative to an axis of a central portion 36. When straightened, the legs 32 and 34 will follow the paths shown in broken-line in FIG. 3B. The distal and proximal legs 32 and 34 will be in their deflected configuration, as shown in FIG. 3B, after implantation so that the legs act as anchors and deforming the vessel geometry, as described elsewhere herein in detail.

An implant 40 having bifurcated ends is shown in FIG. 3C. The implant 40 includes a distal bifurcation 42 which forms a distal anchor and a proximal bifurcation 44 which forms a proximal anchor. The bifurcated ends are joined by a central or middle portion 46 which will usually be straight but may have other configurations as described above with regards to other embodiments. The bifurcations may be constrained to assume closed configurations as shown in broken-line when the implant is in a delivery configuration and will deploy outwardly, as shown in full line, when released from constraint to assume an implanted configuration.

As described thus far, the implants have generally been formed from a single elongate member which is then modified to have anchors at each end. As shown in FIG. 3D, in implant 50 has a distal disc 52 and a proximal disc 54, where the discs will usually be formed from a different material and joined to a separate elongate member 56 which provides a central or middle region of the implant. For example, the central or middle region can be formed from an elastic, metal, or polymer wire as generally described above, while the discs 52 and 54 may be formed from a collapsible polymer, metal, or other material. The discs 52 and 54 will be collapsible, as shown in broken-line, for delivery and will self-deploy to the anchoring configuration, shown in full-line.

An implant 60 having adjustably positionable discs 62 and 64 is shown in FIG. 3E. A distal disc 62 forms the distal anchor and a proximal disc 64 forms the proximal anchor. A central or middle region 66 is typically formed from an elongate member which may be metal, polymer, or any of the forms described above. Unlike the earlier implants, the elongate member which forms the central portion 66 will have a plurality of detents or ratchets 68 spaced-apart along its length. Each of the ratchets or detents 68 will be able to hold the disc in place after deployment. Thus, after the implant 60 has been introduced through the target blood vessel, the degree of closure of the vessel can be adjusted depending on the position of the disc 62 and/or 64 on the shaft of the middle portion 66. It will be appreciated that further components may be provided, such as locks, threads, adhesives, and the like, in order to firmly fix each of the discs 62 and 64 onto the central portion 66 so that the distance between the discs, once selected, will be reliably maintained. Alternatively, at least one of the discs 62 or 64 may be left to be repositionable so that the degree of vessel closure can be adjusted days, weeks, or even longer post-implantation.

Figure 4A:
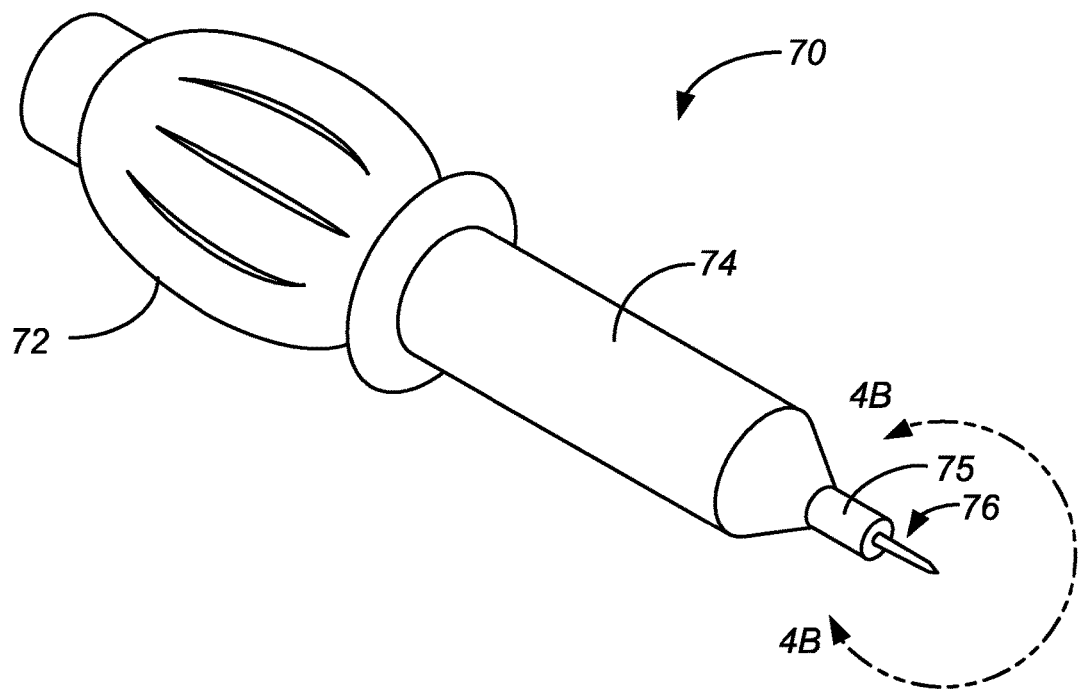
FIGS. 4A and 4B show a first embodiment of an implant delivery system in accordance with the principles of the present invention.
Figure 4B:
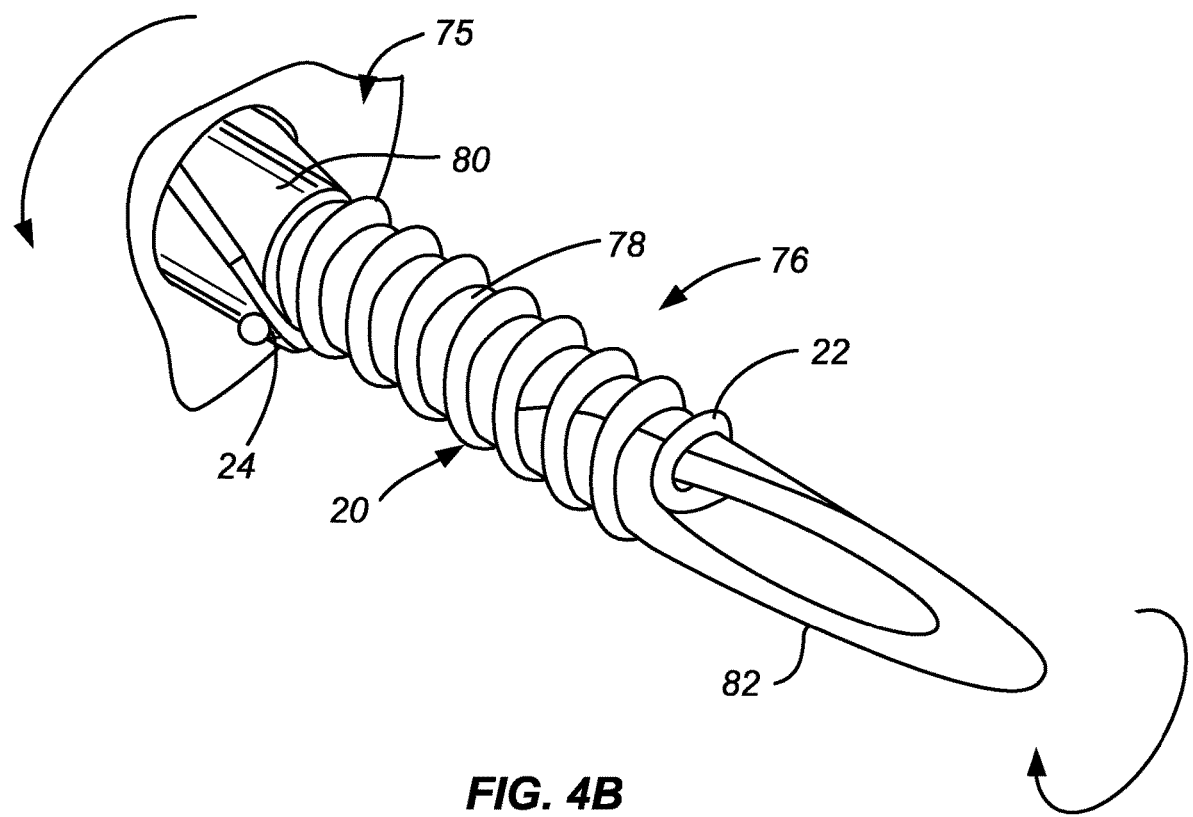

A first exemplary implant delivery device 70 is illustration in FIGS. 4A and 4B. The implant delivery device 70 includes a handle 72, a shaft 74, and a reduced diameter nose portion 75 at a distal end of the shaft. As best seen in FIG. 4B, a cannula assembly 76 extends distally from the nose 75 of the implant delivery device 70, and the cannula assembly includes a needle 78 and a mandrel 80, where the needle and mandrel are rotatable relative to each other. The needle has a sharp tip 82 which allows the cannula assembly 76 to be percutaneously or transcutaneously introduced to and/or across vessels, particularly superficial target veins, such as the dorsal vein as described in detail below. The cannula assembly 76 can carry any of the implants described above. As illustrated, the coil implant 20 is carried with the distal coil 28 removably attached near the sharp tip 82 of the needle and the proximal coil 24 removably attached to the mandrel 80. The removable attachments hold the coil implant 20 in a "constricted" configuration where the elongate body of the implant forms a simple helix extending from the tip of the needle to the distal end of the mandrel. By rotating the needle relative to the mandrel in a first direction, this temporary helical configuration can be tightened over the needle so that the coil remains in place during delivery of the coil, as described in more detail below. By counter-rotating the needle relative to the mandrel, the coil implant 20 may be released from the delivery device 70.

Figure 5:
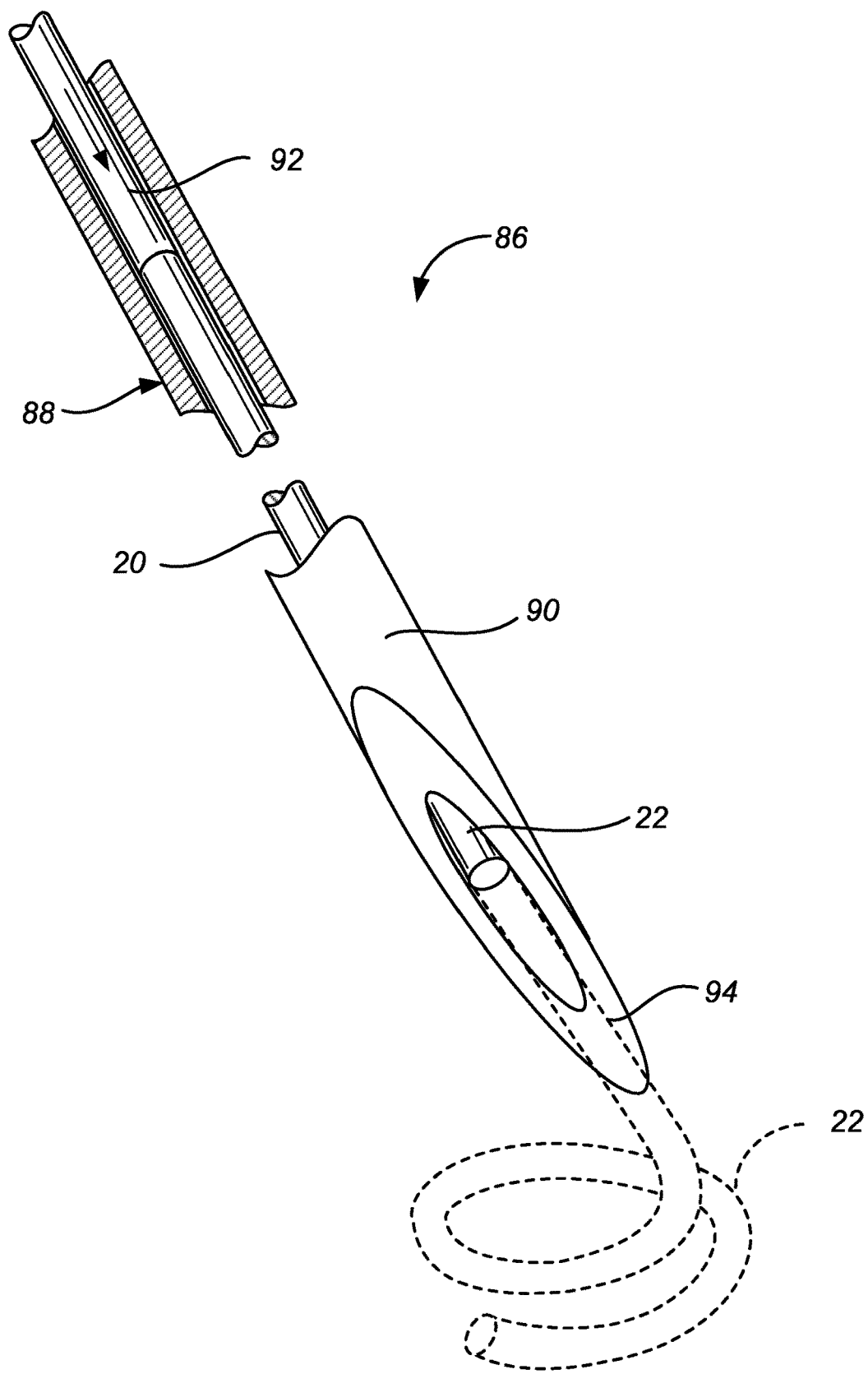
FIG. 5 shows a second embodiment of an implant delivery system in accordance with the principles of the present invention

Referring now to FIG. 5, an alternative implant delivery device 86 is illustrated. Instead of carrying the coil implant 20 over the exterior of the device, as with the first embodiment, delivery device 86 carries the implant in a straightened configuration within a lumen of the device. In particular the implant delivery device 86 comprises a cannula assembly 88 which includes a needle 90 and a pusher 92. The needle 90 has a sharpened distal tip 94 which allows percutaneous or transcutaneous introduction while coil 20 is held within a lumen of the needle. Once in place through the target vessel, pusher 92 can be used to advance the coil 20 to release, at first, the distal coil 22 shown in broken-line. After properly positioning the distal coil 22 relative to the target vessel, the needle may be proximally withdrawn to position the middle region 26 (FIG. 3A) of the coil 20 within the vessel, and thereafter to release the proximal coil 24 over an opposite location on the exterior wall of the vessel.

Referring now to FIG. 6A-6E, use of the implant delivery device 70 for implanting a coil implant 20 in a dorsal vein DV for treatment of erectile dysfunction will be described. The cannula assembly 76 of the delivery device 70 is first positioned adjacent to the dorsal vein DV in a patient's penis P. The dorsal vein DV lies between dorsal arteries DA then above the corpora cavernosa CC. Position of the urethra U is shown for reference.

Figure 6A:
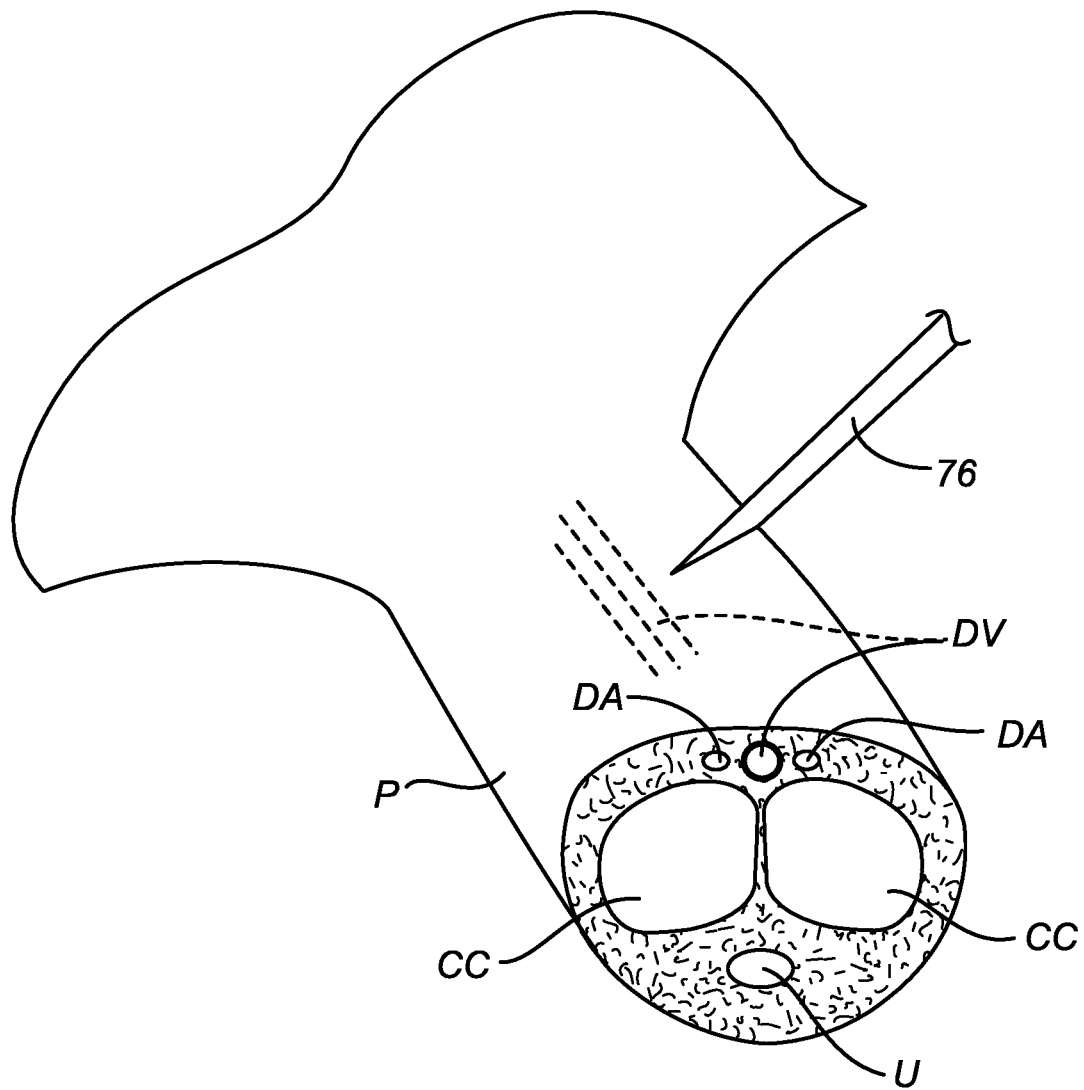
FIGS. 6A-6E show an exemplary method for implanting an implant in a dorsal vein to treat erectile dysfunction using the implant delivery system of FIGS. 5A and 5B.
Figure 6B:
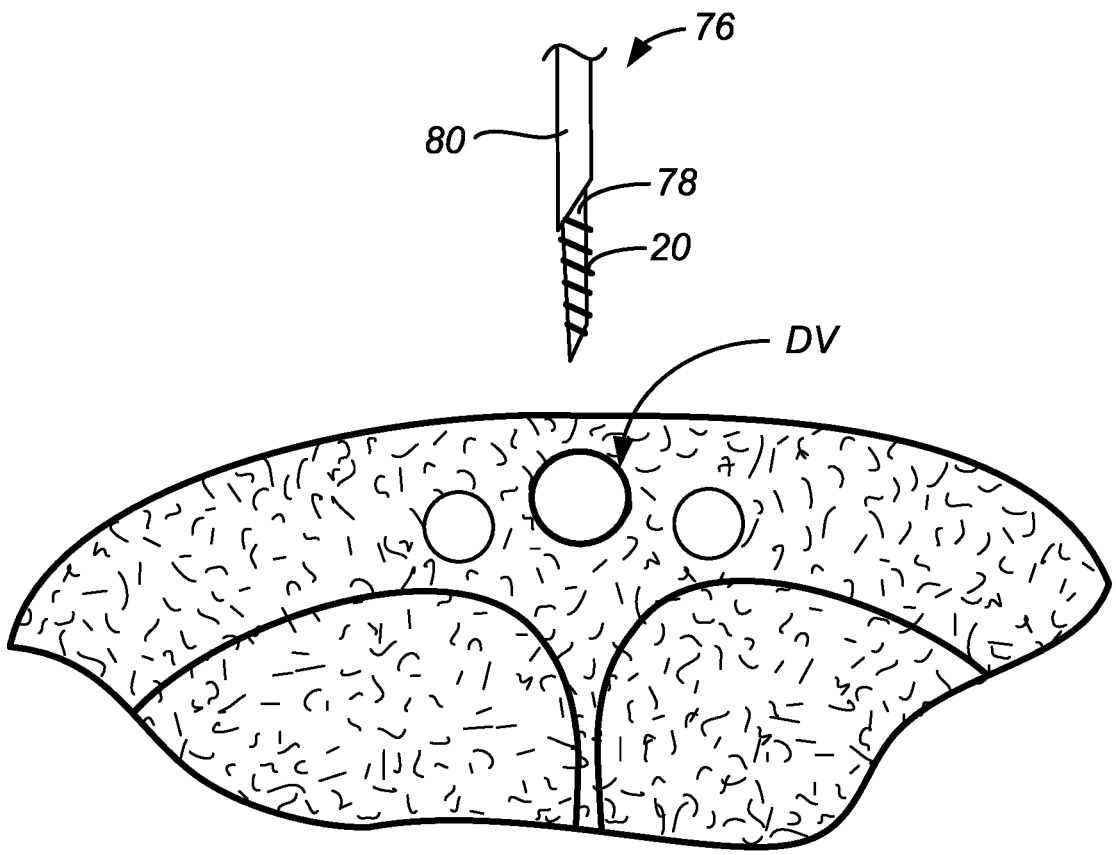
Figure 6C:
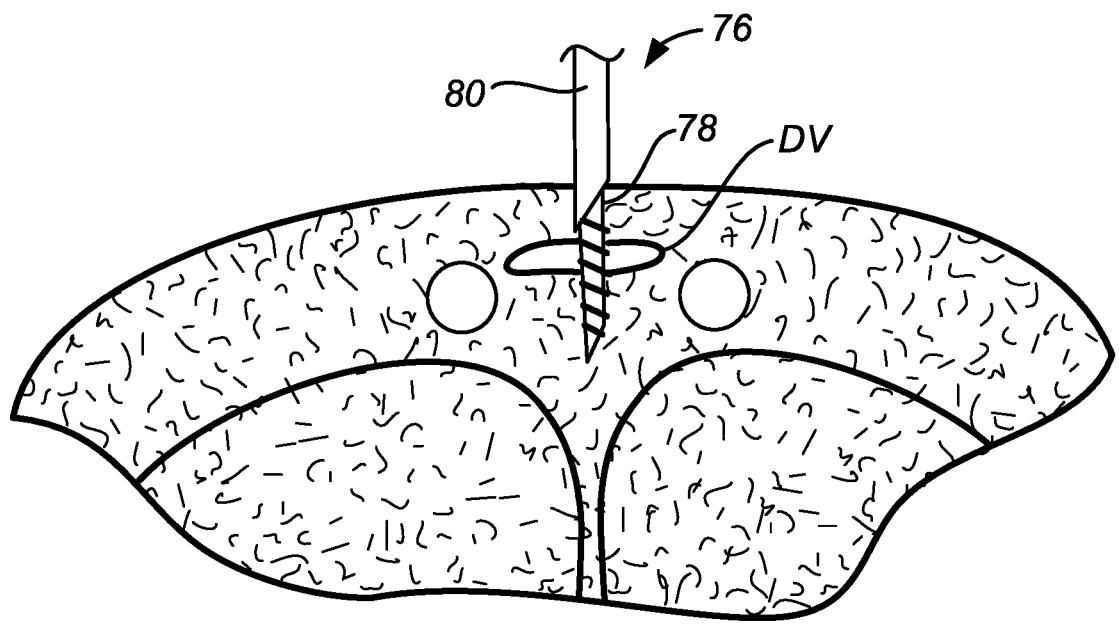
Figure 6D:
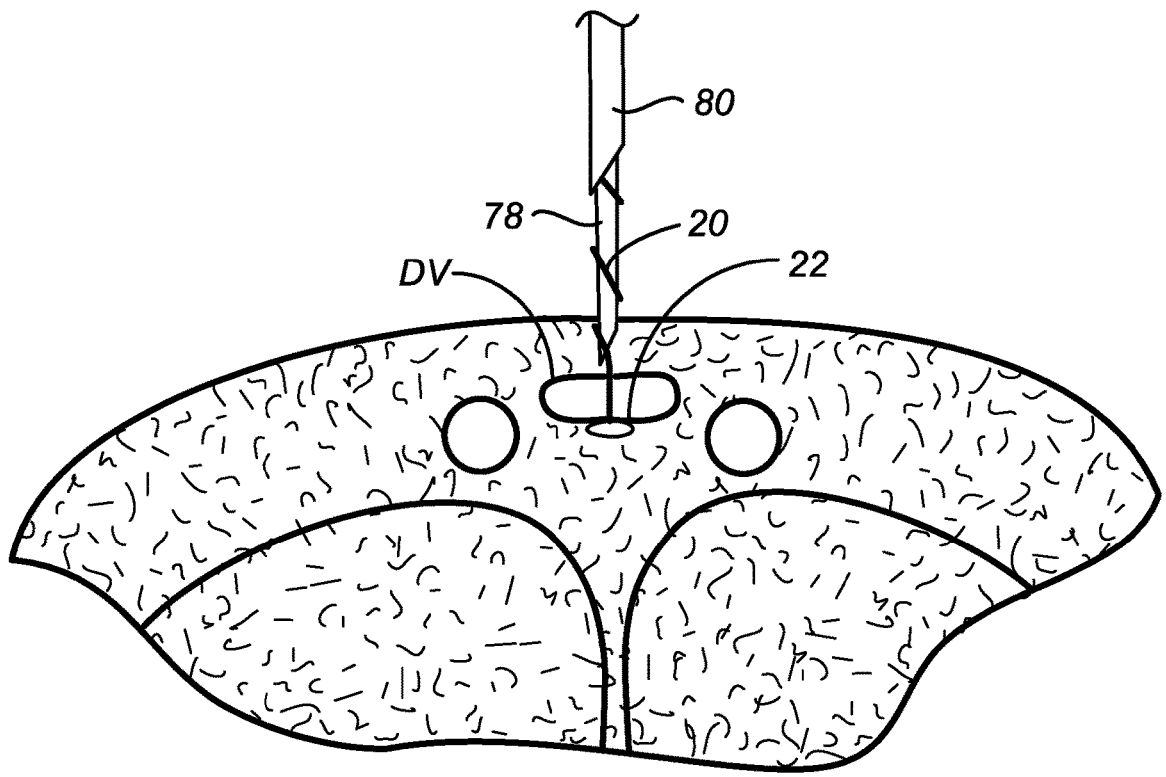
Figure 6E:
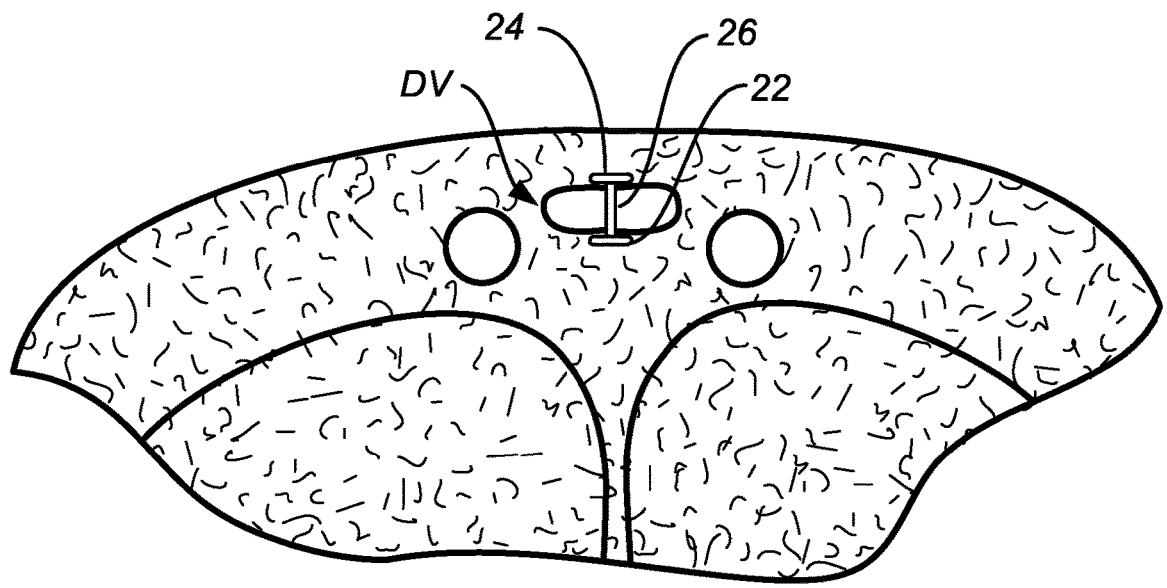

As shown in FIG. 6B, the cannula assembly 76 is aligned with the dorsal vein DV, and the needle 20 is then penetrated distally so that it passes through the dorsal vein DV, as shown in FIG. 6C. Typically, the dorsal vein DV will be at least partially collapsed by the penetrating force of the needle 78. Once the distal tip of the needle is passed the far or distal surface of the dorsal vein DV, the needle 78 will be rotated relative to the mandrel 80 in order to release the distal coil 22, as shown in FIG. 6B. The needle may then be drawn proximally so that the needle overlies the proximal surface of the dorsal vein DV, also shown in FIG. 6D. The needle may then be further rotated relative to the mandrel 80 in order to release the proximal coil 24 over the proximal surface of the vein, as shown in FIG. 6E. The needle may then be completely withdrawn and the procedure can be completed as appropriate for treating such a percutaneous penetration.

While preferred embodiments of the present invention have been shown and described herein; it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for reshaping a native vein to make the vein prone to bending or compression in response to an external force, said method comprising the following steps performed in order:
   penetrating a distal end of a cannula inwardly through an entry location in a wall of the vein and outwardly through an exit location on an opposed wall of the vein, wherein the implant consists of a single wire-like body having a distal coil and a proximal coil, each coil being coiled over an exterior surface of the cannula;
   releasing the distal coil from the exterior of the cannula to expand and anchor the implant on an exterior surface of the opposed wall adjacent to the exit location;
   drawing proximally on the cannula to pull the distal coil against the exterior surface of the opposed wall adjacent to the exit location to partially collapse the lumen of the vein; and
   releasing the proximal coil from the exterior of the cannula to expand and anchor the implant on an exterior surface of the wall adjacent to the entry location to maintain the partial collapse of the lumen of the vein;
   wherein the implant compresses opposed walls of the vein such that a length across a central region of the vein is reduced to less than the diameter of the unconstrained vein but blood flow is not blocked; and
   wherein the compressed shape makes the vein more prone to external forces which cause a decrease or temporary stoppage of blood flow through the vein.

2. A method as in claim 1, wherein the lumen of the vein assumes an ovoid or rectangular shape when compressed by the implant.

3. A method as in claim 1, wherein the implant is constrained in a coiled configuration over an inner needle portion of the cannula while being penetrated and wherein releasing the distal and proximal portions of the implant comprises rotating the needle portion relative to an outer mandrel portion of the cannula.

4. A method as in claim 3, wherein penetrating comprises advancing the needle and cannula assembly through the proximal and distal locations on the wall, wherein the implant is carried over a distal region on the needle.

5. A method as in claim 4, wherein the distal portion of the coiled implant is released from constraint after said distal portion is advanced beyond the exterior surface of the opposed wall adjacent to the distal location.

6. A method as in claim 5, wherein the proximal portion of the coiled implant is released from constraint after the distal portion has been released over the distal location.

7. A method as in claim 1, wherein the implant is anchored in a dorsal vein to treat a patient suffering from erectile dysfunction.

8. An implant delivery system for reshaping a native vein to make the vein prone to bending or compression in response to an external force, said system comprising:

a delivery cannula having an interior passageway and configured to penetrate opposite walls of the vein; and an elastic elongate member consisting of a single wire-like body having a distal end pre-shaped to assume an anchor configuration when released from constraint and a proximal end pre-shaped to assume an anchor configuration when released from constraint;

wherein the distal and proximal ends when in their anchor configurations are configured to be separated by opposed walls of the native vein when the elastic elongate member is implanted in the native vein with each anchor on an exterior surface of a wall of the vein, wherein the anchors compress the opposed walls of the vein to deform the vein wall so that the lumen of the vein assumes an ovoid or rectangular shape but blood flow is not blocked;

wherein the cannula comprises an inner needle and an outer mandrel, wherein the distal end of the elongate member is removably secured to the needle and the proximal end of the elongate member is removably secured to the mandrel so that rotation of the needle relative to the mandrel in a first direction coils the elongate member more tightly over the cannula and rotation of the needle in an opposite direction releases the elongate member from the cannula.

9. An implant as in claim 8, wherein the anchors comprise a coiled distal end and a coiled proximal end separated by a straight middle region.

10. An implant as in claim 8, wherein the anchors comprise a deflected distal end and a deflected proximal end.

11. An implant as in claim 8, wherein the distance between the anchors is selected to be 1.8 mm, 1.5 mm, 1 mm or 0.5 mm.

12. An implant as in claim 11, wherein the wire has a thickness in a range between 10 microns to 1 mm, 20 microns to 0.5 mm, or 30 microns to 0.1 mm.

* * * * *